United States Patent [19]

Crittenden et al.

[11] Patent Number: 4,654,024

[45] Date of Patent: Mar. 31, 1987

[54] THERMORECANALIZATION CATHETER AND METHOD FOR USE

[75] Inventors: James F. Crittenden, Hollis, N.H.; Barry D. Weitzner, Acton, Mass.

[73] Assignee: C.R. Bard, Inc., Murray Hill, N.J.

[21] Appl. No.: 772,364

[22] Filed: Sep. 4, 1985

[51] Int. Cl.⁴ .................. A61M 5/00; A61B 17/36
[52] U.S. Cl. ...................... 604/49; 604/114; 128/303.1; 219/121 LS
[58] Field of Search .............. 604/114, 113, 20, 21, 604/49, 53; 128/303.12, 303.1, 395–398; 219/121 LS

[56] References Cited

U.S. PATENT DOCUMENTS

| 1,615,828 | 2/1927 | Chesney | 128/303.12 |
| 3,301,258 | 1/1967 | Werner et al. | 128/303.1 |
| 4,038,519 | 7/1977 | Foucras | 604/114 L |
| 4,207,874 | 6/1980 | Choy | 604/21 L |

FOREIGN PATENT DOCUMENTS

WO84/04879 12/1984 PCT Int'l Appl. ............ 128/303.1

Primary Examiner—Stephen C. Pellegrino
Attorney, Agent, or Firm—Wolf, Greenfield & Sacks

[57] ABSTRACT

A catheter with a heater mounted on its distal end is used to melt atherosclerotic plaque to clear an obstruction within an artery. The catheter heater is a tapered cone that emits heat from its outer, leading edges. Several embodiments are disclosed in which the power for the heater is generated by electrical resistance heating or by laser energy absorption. In the disclosed method of use, the guidewire is inserted into the lumen of the catheter so that the distal tip of the guidewire extends a few centimeters beyond the heater tip. The catheter is directed into the proper coronary branch by means of the guidewire and the wire is advanced until it meets the obstruction. If the wire can be advanced through the obstruction, the catheter is advanced over the wire until the heater contacts the plaque. The heater is then operated and the catheter is advanced as the plaque melts. If the guidewire cannot be pushed through the obstruction, the guidewire and catheter are advanced together until the obstruction is breached and the guidewire can be extended down the artery. Once a suitable channel has been opened, the catheter is removed and a conventional balloon dilatation catheter is slid over the guidewire to enlarge the stenosis in a conventional manner.

17 Claims, 5 Drawing Figures

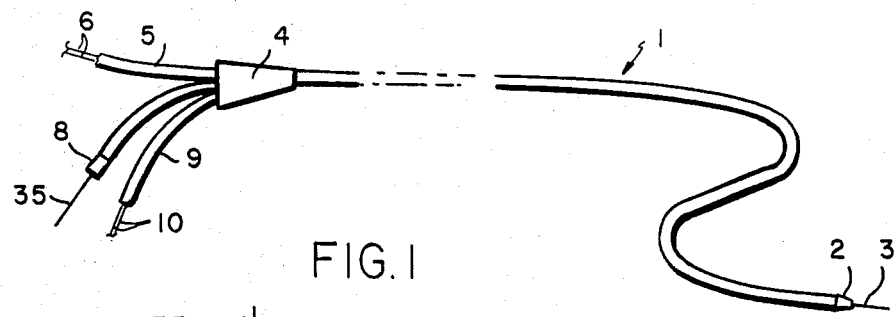
FIG.1
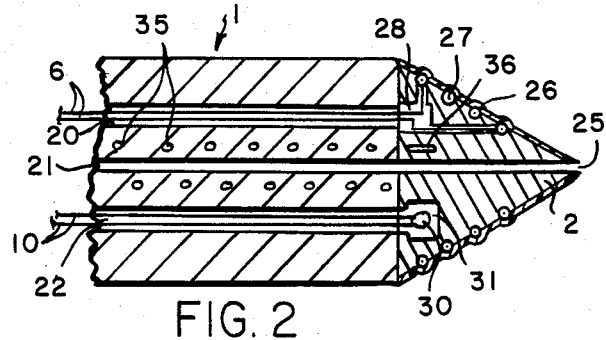
FIG.2
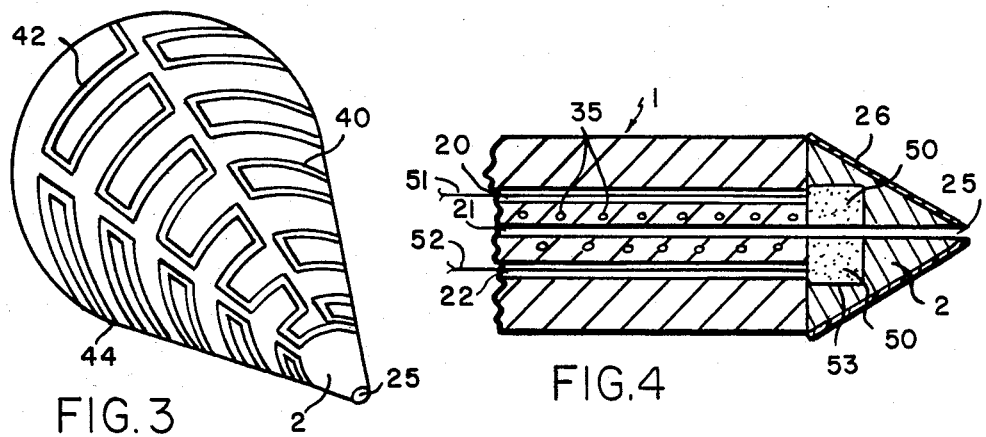
FIG.3
FIG.4
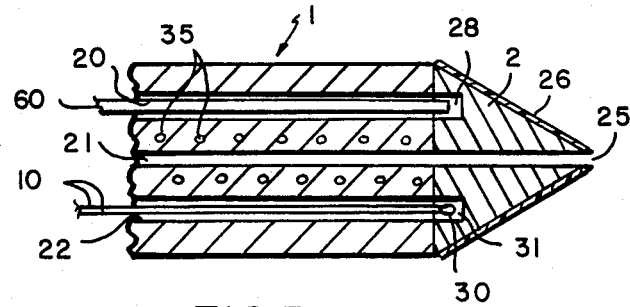
FIG.5

THERMORECANALIZATION CATHETER AND METHOD FOR USE

FIELD OF THE INVENTION

This invention relates to medical instruments which use thermal energy to open an artery blocked by atherosclerotic plaque and, in particular, to instruments which use heat to melt the plaque.

BACKGROUND OF THE INVENTION

Arteriosclerotic coronary artery disease is a common form of heart disease. The disease is caused by a build-up of fibrous and fatty substances on the inner walls of the coronary arteries. The substances combine to form a soft, semi-solid material known as "plaque". Over a period of time the plaque can can become infused with calcium causing it to become hardened. The plaque reduces the size of the lumen in the artery and thereby reduces the blood flow to the heart muscle. If the blood flow is reduced sufficiently, the heart muscle in the area beyond the constriction can be damaged by oxygen starvation resulting in a myocardial infarction, commonly called a heart attack. Alternatively, the plaque build-up may cause turbulence in the blood flow resulting in a thrombosis in the coronary artery, which, in turn, leads to a heart attack.

Direct surgery on the restricted area is often difficult or impossible due to the small size of the affected arteries. Consequently, various procedures have been developed to enlarge atherosclerotic plaque constrictions without requiring incisions in the artery walls, thereby increasing the blood flow to the heart muscle and avoiding heart attacks.

If the stenosis caused by the plaque is not a complete obstruction and if the plaque has a low concentration of calcium (and, therefore, is soft), a dilatation balloon catheter may be used to enlarge the stenosis in the artery. In this conventional procedure, a special catheter with a "balloon" section having expandable walls is inserted into a conveniently located artery and guided through the coronary vasculature to the location of the restriction by means of fluoroscopy and contrast medium injections. The balloon section of the catheter is moved into the constricted area of the artery and pressurized liquid is passed down the catheter to inflate the balloon causing it to expand and compress the plaque against the artery walls. The operation increases the size of the lumen in the artery and therefore increases blood flow.

The dilatation technique, however, does not work where the plaque has a high concentration of calcium and is, therefore, "hard". Also, the technique cannot be used where the plaque has built up to the point where it has formed a complete blockage or where the stenosis is severe and only a very small opening remains, for in these latter situations, the catheter cannot be pushed through the opening.

Accordingly, a number of prior art methods have been devised to open or "recanalize" arteries in areas where the balloon dilatation catheter will not work. In one common method, a catheter is provided with an optical fiber passing along its length. A laser is coupled to the proximal end of the fiber and the laser energy is guided down the fiber and directed onto the plaque to vaporize or melt the plaque. This technique is useful in certain situations, but it suffers from a number of drawbacks.

More particularly, lasers which produce an electromagnetic energy output at a wavelength that is optimally absorbed in the plaque are generally not well-suited to transmission down an optical fiber which requirement is necessary to deliver the laser energy to the area of the constriction. Some lasers are available which do have good tissue absorption characteristics and can be transmitted down an optical fiber, but it is difficult to construct these lasers to generate the required power.

In addition, difficulty is often encountered in constraining the laser energy to the desired area due to scattering. Unless care is used, the interior walls of the artery can be damaged. Such damage can happen, for example, when the laser energy burns through the plaque restriction and then impinges on the artery wall beyond the blockage. For these reasons laser vascular surgery is still in the experimental stages.

As an alternative to laser surgery, another catheter arrangement uses small knives at the distal end to cut away the plaque. This arrangement also suffers from the disadvantages of the balloon dilatation catheter in that it is difficult to use the device in an artery which is tightly constricted.

Accordingly, it is an object of the present invention to provide apparatus for clearing away obstructions in arteries and other blood vessels.

It is another object of the present invention to provide apparatus for clearing obstructions in arteries and other blood vessels which can be used in tightly-constricted blood vessels.

It is a further object of the present invention to provide apparatus which can clear obstructions in arteries and other blood vessels by melting atherosclerotic plaque.

It is yet another object of the present invention to provide apparatus which can remove obstructions in arteries and other blood vessels and which can be advanced along a guidewire that can be easily maneuvered along an artery or other blood vessel.

SUMMARY OF THE INVENTION

The foregoing problems are solved and the foregoing objects are achieved in one illustrative embodiment of the invention which utilizes a catheter with a heater at its distal tip to melt a channel through a plaque obstruction, thereby clearing an obstructed artery. The heater tip has a conical shape and can be heated either electrically or by means of laser energy.

The catheter has a lumen at its center allowing the catheter to be slid over a guidewire, which arrangement allows controlled movement of the catheter through the appropriate vasculature. The guidewire lumen also allows the area in front of the catheter to be flushed with a saline or Ringer's solution before heat is applied to the plaque. Particulate matter generated during the plaque melting process may also be evacuated by means of the guidewire lumen. An additional lumen may be provided in the catheter for electrical connections to a thermal sensor located in the heater tip. The sensor can be connected to a feedback system to control the heater temperature.

Several different methods of manufacturing the heater tip are disclosed. For example, the heater may be comprised of a length of electrical resistance wire, such as nichrome wire, wound around a thermally-insulating core with the temperature of the core being monitored by a resistance temperature detector (RTD) device or a thermocouple. Alternatively, the heater may comprise an etched foil pattern bonded to a substrate cone. Again, the temperature of the etched-foil heater may be controlled by using the RTD properties of the foil or using a conventional thermal sensor feedback control system.

In another embodiment, the heater cone is comprised of resistive epoxy or adhesive. Electrical leads are embedded into the adhesive prior to curing to provide electrical connections. The epoxy or adhesive may be in the shape of a donut that fits into a thermally conducting conical shell or, alternatively, the adhesive itself may be formed into a cone shape. In another embodiment, a conical metal cap is heated by means of laser energy which is carried through the catheter by a fiber optic cable.

In use, the catheter is positioned over a conventional guidewire so that the tip of the guidewire extends a few centimeters beyond the heater tip. The assembly is inserted into the convenient artery by means of a guiding catheter and the guidewire is manipulated to direct the heater catheter into the proper branch of the vasculature. When the guidewire reaches the constricted area, an attempt is made to push the wire down the artery past the stenosis. If the wire is advanced past the stenosis, the heater is then advanced over the wire until it contacts the plaque restriction. The heater is then operated and advanced gently as the plaque softens and melts until the restriction is breached. If the guidewire cannot be pushed across the stenosis, the catheter is slid down the wire until it contacts the blockage. The guidewire and heater are advanced together until the stenosis is breached and the guidewire can be extended out of the heater and down the artery. Once a suitable passageway has been opened, the heater catheter is removed leaving the guidewire. A conventional balloon dilatation catheter is then inserted along the guidewire to enlarge the stenosis and complete the repair procedure.

BRIEF DESCRIPTION OF THE DRAWING

FIG. 1 is an overall view of the laser catheter including the proximal and distal ends.

FIG. 2 is a cross-sectional view of an embodiment of the heater tip using an electrical resistance wire heating element.

FIG. 3 is a perspective view of a conical heater tip using etched foil as the heating element.

FIG. 4 is a cross-sectional view of an additional embodiment utilizing a resistive epoxy heating element.

FIG. 5 of the drawing is a cross-sectional view of another embodiment of the heater tip utilizing laser energy to generate heat.

DETAILED DESCRIPTION OF THE PREFERRED EMBODIMENT

FIG. 1 shows a general drawing of the heater-tipped catheter. Catheter body 1 is comprised of conventional polymeric material and incorporates two or three lumens. The outside diameter of the catheter is similar to standard dilatation catheters to insure compatibility with standard guiding catheters and guidewires. At the distal end of catheter 1 is attached a heater tip 2, to be described in detail hereinafter. Tip 2 is used to concentrate heat directly against the constricting plaque to melt the plaque. Guidewire 3 passes down a central lumen in the catheter and allows control of the placement of the catheter in the vasculature.

At the proximal end of the catheter, a trifurcation fitting 4 is used to divide the two or three lumens into separate ports. One port, 7, which is attached to the lumen that runs down the center of the catheter, is provided with a standard female luer connector. This port allows entry the guidewire 35 and allows connection of the catheter to standard "Y" connectors and injectors. Saline solution may be flushed through this lumen to clear blood from the region in front of the heater tip prior to applying heat to the plaque. Alternatively, particulate matter generated during the heating operation may be evacuated through the central lumen. The lumen will also provide for pressure monitoring and for dye injections to confirm heater position.

The second port 5 which is split off by fitting 4 is used for power connections to the heater or for introduction of an optical fiber in the case of a laser-powered heater. In the case of electrical heater, two wires will be introduced into the port to the heater tip.

The third port, 9, will allow electrical connections to be made to a thermocouple or other temperature monitoring device located in tip 2 in case the catheter is to be used with a standard thermal sensor temperature feedback system. Alternatively, some electrical heaters (which are discussed in detail below) act as resistance temperature detectors (RTDs) and allow monitoring of temperature directly over the electrical power wires. If an RTD type heater is used, the thermal sensor monitor in the third lumen can be eliminated to simplify the construction.

FIG. 2 shows a cross-sectional diagram of an electrically-heated catheter tip which uses the electrical resistance of resistance wire to generate the required heat. Body 1 has three lumens, 20, 21 and 22. The central lumen 21 allows passage of the guidewire through the tip where the wire emerges from orifice 25. Tip 2 is comprised of a thermally-insulating and electrically-insulating material such as alumina ceramic. The resistance heater wire 27 is wound in grooves on the outer surfaces of heater tip 2 (only four grooves are shown for clarity; however, in actual use additional grooves and turns of resistance wire would be used).

The resistance heater wire may be joined to wire leads of lower resistance in order to provide electrical power connections. Such leads are shown in FIG. 2 as leads 6 which travel down the catheter via lumen 20 and terminate in a small cavity 28 in heater tip 2. The cavity contains passages through which lead wires 6 are attached to the ends of resistance wire 27. Alternatively, a single piece of resistance wire may be used to deliver power from the proximal catheter end to the distal catheter end but the portion of the wire wound around the heater tip 2 can be drawn to a smaller diameter in order to produce heating at this point. A third alternative is to extend the resistance wire from heater tip 2 the entire length of the catheter without modification in diameter.

In the embodiments using electrical resistance wire, an electrically insulating material 26, such as epoxy, is used to coat the outside of the heater tip to seal out moisture and provide electrical insulation. An additional cavity 31 is provided in heater tip 2 to house a thermal sensor 30 which is connected to monitoring equipment via leads 10 which pass down the length of the catheter to the proximal end.

Heater tip 2 is attached to catheter body 1 by any of several conventional means, for example tip 2 may be cemented to the catheter body by means of epoxy adhesive. If tip 2 is cemented to body 1 it is desirable to also attach the tip to the body by separate mechanical means so that the tip will not become separated from the body if the attaching adhesive should fail due to tip heating. One way to provide for this mechanical attachment is to provide an additional lumen (not shown) in the catheter body. A wire is then attached to tip 2 and run down this additional lumen to the proximal end of the catheter. The wire prevents the tip from separating from the body. Another, preferred manner of mechanically attaching the tip to the body is to provide a coil of wire having open helical turns 35 which surround the central lumen 21. The wire coils are embedded in the walls of body 1 and the end of the wire 36 is embedded into tip 2. The open coils of wire 35 allow the central lumen 21 to remain open to pass the guidewire (not shown in FIG. 2) yet firmly attach tip 2 to body 1.

In an another embodiment, heat may be produced by using the electrical resistance of an etched foil to create resistance heating. Such an arrangement is shown in FIG. 3 and in this arrangement, heater tip 2 consists of a thermally-insulating and an electrically-insulating substrate (which may be an alumina substrate) to which a thin electrically conductive foil has been bonded. The foil is etched until a plurality of serpentine paths 40, 42 and 44 remain which paths form resistance heating elements. During construction, the foil may be bonded to the substrate before etching or may be etched first and bonded to the substrate cone in a second manufacturing step.

Electrical power leads 6 (as shown in FIG. 2) are connected to opposite ends of the foil serpentine matrix to form an electrical path. With the foil heater arrangement, it is possible to monitor the temperature at the heater tip by taking advantage of the resistance temperature detection (RTD) properties of the foil. Alternatively, a conventional thermal sensor monitoring system such as that shown in FIG. 2 can be used. A layer of electrically-insulating material which coats the outside of the heater tip 2, seals out moisture and electrically insulates the structure completes the assembly. As with the previous embodiment, a lumen, 25, passing through the center of the substrate cone allows passage of a guidewire to direct the catheter to the blockage site.

As with the previous embodiment, tip 2 is mechanically attached in a manner described above to the catheter body to prevent physical separation.

FIG. 4 shows a cross-sectional view of an additional embodiment of the heater catheter in which the heat is generated by passing electrical current through a resistive epoxy or adhesive. In the embodiment shown in FIG. 4, the catheter has the same mechanical construction as the previous embodiments but heater tip 2 is comprised of a thermally-conductive shell. Tip 2 has a cavity 53 in the rear portion into which fits a toroidal-shaped piece of epoxy 50. The electrical leads 51 and 52 are embedded in the epoxy before curing to form an electrical connection to the heater unit. After curing, the resistance of the epoxy material can be precisely adjusted by trimming the cured adhesive until the desired value is reached. As with the previous embodiments, temperature monitoring can be accomplished by using either resistance temperature detector (RTD) properties of the adhesive or a conventional thermal sensor monitoring system. Alternatively, the resistive adhesive can be formed into a cone shape with a hole 25 is drilled through the center of the cone to accommodate the guidewire.

An electrically-insulating, thermally-conductive coating 26 encapsulates the cone to provide a seal for moisture and to electrically insulate the apparatus.

In yet another embodiment of the invention, shown in FIG. 5, heat is generated at the heater tip by allowing a laser beam to impinge on a thermally-conductive cone 2. A material suitable for cone 2 would be a metal such as stainless steel. The cone may also incorporate radiopaque markers in order to make it easier to locate once it is in the patient. In this embodiment, laser energy, generated by a laser located at the proximal end on the fiber, is carried by an optical fiber 60 which passes down the a lumen 20 which extends the length of the catheter. The distal end of the fiber fits into a cavity 28 in catheter tip 2. Cavity 28 is a blind cavity which ensures that no laser energy escapes from the catheter end. As with previous embodiments, an additional cavity 31 may be provided to house a thermal sensor 30. Thermal sensor 30 is connected, via wires 10, to the proximal end of the catheter and used for temperature monitoring purposes. A thermally-conductive, coating 26, completes the assembly.

In use, prior to inserting the catheter into the patient, the catheter is slid over a conventional catheter guidewire so that the tip of the guidewire extends a few centimeters beyond the heater tip. The catheter and guidewire assembly is inserted into the convenient artery by means of a guiding catheter which has been previously prepared in a conventional manner. Using fluoroscopy while injecting radiopaque dye through the guidewire lumen, the guidewire is manipulated to direct the heater catheter into the proper branch of the vasculature. The catheter has been designed to be sufficiently small to operate in the confined spaces of the coronary vasculature, but may be used in other areas where plaque restrictions have become a problem. When the guidewire reaches the constricted area, an attempt is made to push the wire down the artery past the stenosis. If the wire is advanced past the stenosis, the heater is then slid over the wire until it contacts the plaque restriction. The heater is then turned on. The temperature of the heater is controlled by the temperature monitoring system so that the heater tip stabilizes at a temperature which is sufficiently hot to melt the plaque but not hot enough to vaporize the plaque, which would complicate material removal. It has been found that a temperature in the range 120° C. to 180° C. is satisfactory in the illustrative embodiment. When the heater is operated, the catheter is advanced gently as the plaque softens and melts until the restriction is breached. Particulate matter from the melted plaque can be removed by suction through the guidewire lumen.

If the guidewire cannot be pushed across the stenosis, the catheter is slid down the wire until it contacts the blockage. The guidewire and heater are advanced together until the stenosis is breached and the guidewire can be extended out of the heater and down the artery. Once a suitable passageway has been opened, the heater is turned off and allowed to cool. After the heater has cooled, the catheter is removed leaving the guidewire projecting through the restriction. A conventional balloon dilatation catheter is then slid along the guidewire to the restricted area and operated in the conventional manner to enlarge the stenosis and complete the repair procedure.

What is claimed is:

1. A catheter for breaching a restriction in an artery caused by atherosclerotic plaque, said catheter comprising,
   a catheter body having a proximal end and a distal end and a lumen passing through the center thereof and extending along the length thereof for accepting a guidewire,
   a heater attached to said distal end, said heater comprising,
   a cone having a base attached to said distal end, said cone having a hole therethrough extending perpendicularly to said base through the center of said cone to allow passage of a guidewire,
   means for heating the sloping surface of said cone to a temperature sufficient to cause said plaque to melt and
   means responsive to the temperature of said sloping surface for returning a signal having a value related to the temperature of said sloping surface to the proximal end of said catheter body.

2. A catheter for breaching a restriction in an artery according to claim 1 further comprising a thermally-conductive, electrically-insulating coating on the surface of said cone.

3. A catheter for breaching a restriction in an artery according to claim 1 wherein said heating means comprises a length of electrical resistance wire wound on a thermally-insulating and electrically-insulating core.

4. A catheter for breaching a restriction in an artery according to claim 1 wherein said heating means comprises an etched foil heating element bonded to a thermally-insulating and electrically-insulating cone.

5. A catheter for breaching a restriction in an artery according to claim 1 wherein said cone is comprised of electrically-resistive epoxy and said heating means comprises means for connecting said cone to an electrical power source.

6. A catheter for breaching a restriction in an artery according to claim 1 wherein said cone is comprised of thermally-conductive material and said heating means comprises means for causing the output from a laser to impinge on said cone.

7. A catheter for breaching a restriction in an artery according to claim 1 wherein said heating means further comprises means for providing power to said cone to heat said cone, means responsive to the temperature of said cone for generating a temperature signal and means responsive to said temperature signal for controlling the amount of power provided to said cone.

8. A catheter for breaching a restriction in an artery according to claim 7 wherein said means for generating said temperature signal comprises a thermocouple.

9. A catheter for breaching a restriction in an artery according to claim 7 wherein said means for generating said temperature signal comprises a resistance temperature detector.

10. A catheter for breaching a restriction in an artery caused by atherosclerotic plaque, said catheter comprising,
    a catheter body having a proximal end and a distal end and having a first, a second and a third lumen passing through, said first lumen passing through the center of said catheter and extending along the length thereof for accepting a guidewire,
    a heater attached to said distal end, said heater comprising,
    a cone having a base attached to said distal end, said cone having a hole therethrough extending perpendicularly to said base through the center of said cone to allow passage of a guidewire, and
    a heater located in said cone for heating the sloping surface of said cone to a temperature sufficient to cause said plaque to melt,
    means passing through said second lumen for providing power to said heater,
    means responsive to the temperature of said cone for generating a temperature signal, and
    means responsive to said temperature signal for sending a feedback signal through said third lumen to the proximal end of said catheter.

11. A catheter for breaching a restriction in an artery according to claim 10 further comprising a thermally-conductive, electrically-insulating coating on the surface of said cone.

12. A catheter for breaching a restriction in an artery according to claim 10 wherein said heater comprises a length of electrical resistance wire wound on a thermally-insulating and electrically-insulating core.

13. A catheter for breaching a restriction in an artery according to claim 10 wherein said heater comprises an etched foil heating element bonded to a thermally-insulating and electrically-insulating cone.

14. A catheter for breaching a restriction in an artery according to claim 10 wherein said cone is comprised of electrically-resistive epoxy and said heater comprises means for connecting said cone to an electrical power source.

15. A catheter for breaching a restriction in an artery caused by atherosclerotic plaque, said catheter comprising,
    a catheter body having a proximal end and a distal end and having a first, a second and a third lumen passing through, said first lumen passing through the center of said catheter and extending along the length thereof for accepting a guidewire,
    a heater attached to said distal end, said heater comprising,
    a cone having a base attached to said distal end,
    said cone having a hole therethrough extending perpendicularly to said base through the center of said cone to allow passage of a guidewire and said cone being comprised of thermally-conductive material,
    a heater located in said cone for heating the sloping surface of said cone to a temperature sufficient to cause said plaque to melt, said heater comprising means for causing the output from a laser to impinge on said cone,
    means passing through said second lumen for providing power to said heater,
    means responsive to the temperature of said cone for generating a temperature signal, and
    means responsive to said temperature signal for sending a feedback signal through said third lumen to the proximal end of said catheter.

16. A catheter for breaching a restriction in an artery according to claim 15 wherein the output of a laser is conveyed from the proximal end of said catheter to the distal end of said catheter by means of an optical fiber passing through said second lumen.

17. A method for breaching a restriction in an artery caused by atherosclerotic plaque by means of a catheter having a heating tip and a lumen therethrough for accepting a guidewire, said method comprising the steps of:

A. positioning said catheter over said guidewire so that the tip of the guidewire extends a few centimeters beyond the tip of said catheter,
B. inserting the catheter and guidewire into a patient's artery by means of a guiding catheter,
C. manipulating said guidewire to direct the heater catheter into the proper branch of the vasculature,
D. when said guidewire reaches the restricted area, pushing said guidewire down the artery past said restriction,
E. advancing said catheter over said guidewire until said heating tip contacts said restriction,
F. operating said heating tip,
G. advancing said catheter as the plaque softens and melts until said restriction is breached,
H. removing said catheter by sliding it over said guidewire leaving said guidewire in place, and
I. inserting a balloon dilatation catheter along said guidewire to enlarge the stenosis and complete the repair procedure.

* * * * *